US005576452A

United States Patent [19]
Dever et al.

[11] Patent Number: 5,576,452

[45] Date of Patent: Nov. 19, 1996

[54] CONTINUOUS PROCESS FOR THE PRODUCTION OF A ZINC CONTAINING CHEMICAL PRODUCT

[75] Inventors: James L. Dever, Medina; Anthony F. Guerini, Jr., Aurora, both of Ohio

[73] Assignee: Ferro Corporation, Cleveland, Ohio

[21] Appl. No.: 520,581

[22] Filed: Aug. 29, 1995

[51] Int. Cl.$^6$ .......................................... C07F 3/06
[52] U.S. Cl. ................................. 556/130; 524/382
[58] Field of Search .................. 556/130, 76, 108, 556/113, 146, 181, 83

[56] References Cited

U.S. PATENT DOCUMENTS

| | | | |
|---|---|---|---|
| 2,918,451 | 12/1959 | Elliott | 524/332 |
| 3,455,995 | 7/1969 | Bowman et al. | 556/76 |
| 4,498,783 | 2/1985 | Rudolph | 366/132 |
| 4,544,279 | 10/1985 | Rudolph | 366/132 |
| 4,605,444 | 8/1986 | Wiedmann et al. | 106/138 |
| 4,732,775 | 3/1988 | Millauer | 426/635 |
| 4,746,529 | 5/1988 | Rapp | 426/660 |
| 4,760,129 | 7/1988 | Haering et al. | 528/481 |

FOREIGN PATENT DOCUMENTS

WO9307208  4/1993  WIPO.

OTHER PUBLICATIONS

WO89/09758 published Oct. 19, 1989 Hallsworth et al.
WO92/09549 published Jun. 11, 1992 (BOS).
WO94/10113 published May 11, 1994 (BOS et al).
WO93/07208 published Apr. 15, 1993 (Dever et al).

*Primary Examiner*—Veronica P. Hoke
*Attorney, Agent, or Firm*—Rankin, Hill, Lewis & Clark

[57] ABSTRACT

The present invention provides a continuous melt process for the preparation of a zinc oxide/pentaerythritol chemical product comprising the steps of providing a continuous processor having a product feed zone, a reaction zone, and a discharge zone.

14 Claims, No Drawings

CONTINUOUS PROCESS FOR THE PRODUCTION OF A ZINC CONTAINING CHEMICAL PRODUCT

TECHNICAL FIELD

The present invention provides a continuous process for the production of a chemical product. More particularly, the present invention provides a process for producing a new zinc containing chemical product using a continuous melt processor.

BACKGROUND

Continuous melt processes are utilized to produce a variety of products ranging from chocolates to plastics. In some situations, a continuous melt process can afford one or more benefits as compared to a noncontinuous or batch-type process. Such benefits include improved yields, faster processing times, decreased production costs and improved products.

Many continuous processes are performed using an extruder. For example, Haering et al. U.S. Pat. No. 4,760,129 discloses a process of preparing polyamides (Nylon) using an extruder. Rapp U.S. Pat. No. 4,746,529 discloses a process for producing chocolate using an extruder. Wiedmann et al. U.S. Pat. No. 4,605,444 discloses a process for the production of caseinates using an extruder.

The present invention provides a new and improved continuous melt process for use in producing a new zinc oxide/pentaerythritol chemical product wherein the product of the process is much improved as compared to zinc oxide and pentaerythritol physical blends as disclosed in Elliott U.S. Pat. No. 2,918,451, and zinc oxide/pentaerythritol products produced using batch processes as disclosed in WIPO publications WO 93/07208 to Ferro Corporation and WO 94/10113 to Unichema Chemie B.V. Applicants believe that the chemical product of the present invention is improved because the new process provides carefully controlled time at temperature which in turn provides better process and quality control, yielding a vastly improved chemical product.

SUMMARY OF THE INVENTION

The present invention provides a new and improved method of making a chemical product which product displays greatly improved properties as compared to product made using the noncontinuous or batch-type processes of the prior art.

In one aspect of the invention there is provided a process for the preparation of a zinc oxide/pentaerythritol chemical product comprising the steps of providing a continuous melt processor having a raw material feed zone, a reaction zone, and a discharge zone; feeding zinc oxide and pentaerythritol into the raw material feed zone and providing a raw material mixture comprising the zinc oxide and the pentaerythritol; maintaining a melt temperature of from about 185° C. to about 245° C. in the reaction zone; maintaining a temperature of from about 185° C. to about 245° C. in the discharge zone; transporting the raw material mixture into the reaction zone and maintaining a residence time for the raw material mixture in the reaction zone of from about 10 to about 60 seconds so as to provide a reacted chemical product; transporting the reacted chemical product into the discharge zone; and removing the reacted chemical product from the discharge zone.

The product of the above process can be used to produce excellent stabilizer compositions for use in stabilizing aliphatic chlorine containing polymers such as poly(vinyl chloride) (PVC). As used in this specification and the claims below the term "aliphatic chlorine containing polymers" means any polymer which contains one or more aliphatic chlorine substituents. Such aliphatic chlorine polymers include in addition to PVC, which represents a major application, for example, HYPALON (chlorosulfonated polyethylene), neoprene (polychloroprene), chlorinated polyethylene, and polyvinylidene chloride. These aliphatic chlorine containing polymers may be used alone, or with other polymers to form alloys or blends.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION

The present invention provides a new and improved process that provides a new and improved zinc containing chemical product. The chemical product, when used as an additive for aliphatic chlorine containing polymers, yields vastly improved heat stabilizer performance and better retention of electrical properties as compared to conventional zinc oxide/pentaerythritol additives. Since the chemical product of the present invention provides better performance, lower loading levels are permitted resulting in better cost performance. Furthermore, the chemical product of the present invention allows for the production of lead-free commercial wire products, something that was not at all possible by the use of conventional or prior art zinc oxide/pentaerythritol additives. Also, the product of the present invention consistently maintains its properties over an extended shelf life.

The continuous process of the present invention employs a continuous melt processor. A continuous melt processor includes, but is not limited to, the following types of equipment:
1. Farrel Continuous Mixers; and
2. Buss-Condux Co-kneaders; and
3. Werner-Pfleiderer Twin Screw Extruders; and
4. Teledyne Melt Processors.

The continuous melt processor may also comprise a conventional single screw extruder. However, a twin screw extruder is generally preferred. A twin screw extruder is generally preferred because of its ability to provide better mixing as compared to a single screw extruder.

Whatever type of equipment is used in the process of the present invention, there are several basic requirements for the equipment. Specifically, the equipment must include a raw material feed zone, a reaction zone, and a discharge zone. The reaction zone must include temperature control (e.g., water cooling or heating elements) so as to allow one to control the temperature of the reaction melt. Further, the reaction zone must have the ability to mix the materials being processed and the ability to transport such materials from the feed zone to the discharge zone in a controlled period of time.

The reaction zone is maintained at such a temperature that the materials being processed attain a melt temperature of from about 185° C. to about 245° C. and convert the zinc oxide and pentaerythritol to a reacted chemical product. As referred to herein, unless otherwise indicated, temperatures refer to the temperature of the materials being processed, not the temperature of the processing equipment or its components such as, for example, the barrel or the screw. The materials being processed are held in the reaction zone for a period of from about 10 to about 60 seconds. Of course, it will be appreciated that the most preferred time and temperature utilized will be dependent on such factors as feed rates, mixing and shear rates, barrel sizes, etc. However, if the materials being processed are subjected to temperatures below 185° C., or temperatures above 245° C., one will be outside the processing window and the proper chemical product will not be produced. Further, if the materials being processed spend too much or too little time in the reaction zone, the proper chemical product will not be produced.

Once the zinc oxide and pentaerythritol are reacted, the reacted materials are sent or transported to the discharge zone which preferably is maintained at a temperature of from about 185° C. to about 245° C. Care must be taken to control and generally minimize the amount of time the reacted materials spend in the heated discharge zone. Thus, the materials being processsed must not spend more than about 70 seconds combined in the reaction and discharge zones. After the discharge zone, the chemical product is transported or fed to a device which converts the material into a convenient handleable form. Such devices include, for example, chilled roll flakers, chilled belt flakers, and similar conventional equipment.

The reaction of the zinc oxide and the pentaerythritol produces several by-products including water and aldehydes. Thus, preferably, either or both of the reaction zone and the discharge zone include some type of a vent to allow the volatile by-products to escape during the reaction of the zinc oxide and pentaerythritol.

If one does not have a continuous melt processor with automatic feeders, the zinc oxide and pentaerythritol should be preblended prior to being fed into the raw material feed zone of the continuous processor. Alternatively, instead of premixing the zinc oxide and pentaerythritol, one can employ a continuous melt processor that includes a pair of automated feeders that automatically supply optimum ratios of the zinc oxide and pentaerythritol to the reaction zone.

The pentaerythritol is preferably utilized with zinc oxide at a rate of about 1.7 to about 2.3 moles of pentaerythritol for every mole of zinc oxide. High quality, pure, commercial grades of zinc oxide are preferred in the present process. Technical grades of pentaerythritol that contain minor amounts of higher pentaerythritol polyols are preferred in the present process. An example of a suitable product is STAY-FLAME 88 pentaerythritol available from U.S. Chemicals. No undesirable contaminants should be added to the process. Thus, the zinc oxide and pentaerythritol processed in the reaction zone should be substantially free of any other undesirable reactive chemicals or materials.

The chemical product or material produced by the present invention displays numerous advantages over zinc oxide/pentaerythritol materials produced by prior art methods. Specifically, the chemical product of the present invention displays better stabilization activity, is more resistant to the detrimental effects of moisture and it has much better electrical properties. The chemical product of the present invention can be used as a stabilizer additive in various applications including rigid pipe, injection molded parts, electrical wire and cable, seals, calendaring, automotive applications, appliance parts, roofing materials, flooring and general flexible and semirigid applications.

The chemical product of the present invention provides a stabilizer system that displays a volume resistivity in PVC resin after aging for 26 weeks at 70° C. and 70% relative humidity of at least $1.0 \times 10^{14}$ Ohms·cm pursuant to the test procedures of ASTM D257(1994). Pursuant to this test procedure 3.5% by weight of the zinc oxide/pentaerythritol chemical product along with other conventional additives (defined below immediately prior to the Examples) is added to PVC resin via compounding. Samples are then prepared and subjected to 26 weeks of aging at 70° C. and 70% relative humidity. The test procedures of ASTM D257(1994) are incorporated herein by reference.

The chemical product of the present invention serves as a primary heat stabilizer system for aliphatic chlorine containing polymers. The stabilized polymer blend may also include conventional co-stabilizer additives, such as, for example, tris-(2-hydroxyethyl) isocyanurate (THEIC), a magnesium salt of an organic carboxylic acid, a calcium salt of an organic carboxylic acid, a barium salt of an organic carboxylic acid and a polyol. The polymer blend may contain less than 0.01% by weight zinc stearate, lead or tin depending on the specific application. Additionally, depending upon the particular application, the polymer blend is substantially free of zinc stearate, lead or tin.

The polymer blend may include one or more fillers such as titanium dioxide ($TiO_2$), clay, talc, calcium carbonate, glass, silicates, etc. The polymer blend may also include a plasticizer. A plasticizer is defined herein as any material that when added to the blend reduces the glass transition temperature of the polymer. Examples of plasticizers include, for example, chlorinated paraffins, waxes, benzoates, phthalates such as dioctyl phthalate, glycerates, epoxidized soybean oil and trialkyl trimellitate. The polymer blend may also include an impact modifier that enhances the impact properties of the polymer blend. Suitable impact modifiers include, for example, methacrylate butadiene (MBS), acrylic polymers, ABS, chlorinated polyethylene (CPE) and ethylene vinyl acetate (EVA). The polymer blend may also include a processing aid that serves to ease the transition from raw PVC resin to the finished product. Suitable process aids include, for example, acrylic copolymers. Other conventional additives may be included in the polymer blend such as flame retardants and pigments or colorants.

The present invention also provides a method of producing a stabilized aliphatic chlorine containing polymer blend using the zinc oxide/pentaerythritol chemical product. The method includes the steps of providing an aliphatic chlorine containing polymer; providing a stabilizer system comprising the zinc oxide/pentaerythritol chemical product; and mixing the aliphatic chlorine containing polymer with the stabilizer system to form the stabilized aliphatic chlorine containing polymer blend comprising at least about 0.01% by weight zinc oxide/pentaerythritol chemical product. Preferably, the stabilized aliphatic chlorine containing polymer blend comprises at least about 0.05% by weight zinc oxide/pentaerythritol chemical product. More preferably, the stabilized system comprises from about 0.1% by weight to about 10% by weight zinc oxide/pentaerythritol chemical product.

During the mixing step the aliphatic chlorine containing polymer and the stabilizer system are preferably mixed at a temperature of at least about 240° F. for at least about 2 minutes. It will be appreciated that the preferred compounding temperatures and times are a function of such variables as the type of processing equipment utilized, the particular resin being processed and the degree of plasticization required. WIPO publication WO 93/07208 (International Application Number PCT/US92/08682) to Ferro Corporation is incorporated herein by reference, and specifically for its teachings as to how one can utilize a zinc containing stabilizer in various types of polymers and in conjuction with other additives.

The invention further provides a stabilizer system for use in stabilizing aliphatic chlorine containing polymers, the stabilizer system comprising at least about 0.05% by weight zinc oxide/pentaerythritol chemical product. Preferably, the stabilizer system comprises from about 0.05% by weight to about 95% by weight zinc oxide/pentaerythritol chemical product.

As used in this specification and the claims below the term "stabilizer system" is intended to be afforded as broad of an interpretation as possible such that it also encompasses stabilizers sold, utilized or provided as multiple individual components or blended together in a single formulation or composition.

The following Examples will serve to illustrate the novel features and advantages of the present invention. While these examples will show one skilled in the art how to operate within the scope of this invention, they are not to serve as a limitation on the scope of the invention for such scope is only defined in the claims below.

In Examples IV and V where polymer blends are produced, such blends comprise by weight 100 parts ASTM 5(1994) PVC resin, 40 parts trioctyl trimellitate, 10 parts fully calcined clay, 15 parts ground calcium carbonate, 0.25 parts stearic acid and 6 parts of the indicated zinc oxide/pentaerythritol stabilizer system (i.e., a stabilizer system based on the chemical product of the present invention, a physical blend or the prior art complex as indicated). In each case the stabilizer system comprises by weight percent 60.85% of the applicable zinc oxide/pentaerythritol compound or blend, 8.52% calcium benzoate, 4.26% dipentaerythritol, 6.09% bisphenol A, and 20.28% magnesium oxide.

Example I

Premixed zinc oxide and pentaerythritol, at a ratio of 2 moles of pentaerythritol for every mole of zinc oxide is fed into a Werner-Pfleiderer ZSK-40 corotating twin screw extruder. The screw for the machine includes 1/6 conveying elements, 1/6 devolitization elements, 1/6 shear elements and 1/2 heavy mixing elements.

The screw is set at a speed of 300 rpm with an output of 175 lbs per hour. Residence time in the reaction zone or heated portion of the screw is 20 seconds at a melt temperature of about 220° C. The discharge zone of the extruder is maintained at the necessary temperature so as to provide a melt temperature of about 200° C., and residence time for the reacted material in the discharge zone is less than about 10 seconds.

Reacted material from the discharge zone is fed onto a metal cooling belt with a crush roll near the front of the belt. The crush roll is far enough down the length of the belt so that the belt is solidified into a hard, brittle mass which is reduced in size to an average particle of about 150 microns.

Example II

Premixed zinc oxide and pentaerythritol, at a ratio of 2 moles of pentaerythritol for every mole of zinc oxide is fed into a 5 inch Teledyne continuous mixer. The Teledyne includes a working barrel of 22 inches with 1/6 of the barrel serving to convey, 1/6 serving to shear, and 2/3 of the barrel serving to heavy mix. The screw is run at 150 rpm with an output of 450 pounds/hour. The Teledyne includes a headgate which is set at 5/32 inches open. The residence time is held to 12 seconds in the reaction zone. The reaction zone of the Teledyne mixer is held at a temperature so as to provide a melt temperature of about 220° C., and the reacted material has a residence time in the discharge zone of less than about 10 seconds. The discharge zone of the screw is maintained at temperature so as to provide a melt temperature for the reacted material of about 220° C.

Reacted material from the discharge zone is fed into a two-roll crusher-flaker to provide an average particle of about 150 microns.

Example III (Comparative)

Volume resistivity tests were run direct (i.e., with no compounding of the product into a resin) on the product of Examples I and II, and on a zinc oxide/pentaerythritol (1:2 molar ratio) product made by a conventional batch process and a conventional physical blend of the same ratio. As shown below, the products of Examples I and II displayed superior results. The volume resistivity was run using the ASTM D257 procedure. However, because the samples were powders, the test procedure had to be modified using a sample holder developed and described in NASA Tech Briefs, page 58, November 1991 issue. The term "modified test procedure ASTM D257(1994)" means the test procedures of ASTM D257(1994) modified by using the sample holder described in NASA Tech Briefs, page 58, November 1991 issue. The samples were aged for 26 weeks at 70° C. and 70% relative humidity. The chemical product of the present invention displays a volume resistivity (without aging) pursuant to modified test procedure ASTM D257(1994) of at least $2 \times 10^{12}$ Ohm·cm.

| Sample | $VRX10^{12}$ (No Aging) | $VRX10^{12}$ (Aged) |
| --- | --- | --- |
| Example I | 3.8 | 1.0 |
| Example II | 4.8 | 0.9 |
| Conventional batch process (1 mole ZnO:2 moles pentaerythritol) | 1.2 | 0.1 |
| Physical blend (1 mole ZnO:2 moles pentaerythritol) | 0.8 | * |

*not measurable

Example IV (Comparative)

Stabilizer systems based on the products of Examples I and II, and conventional zinc oxide/pentaerythritol batch products and physical blends as used in Example III, were added via compounding into PVC resin. The modified PVC was then aged for 26 weeks at 70° C. and 70% relative humidity. Volume resistivities were run pursuant to ASTM D257(1994). As shown below, stabilizer systems based on the products of Examples I and II displayed superior results. A product that provides a stabilizer system which yields a volume resistivity below $1 \times 10^{14}$ Ohms·cm is wholly unacceptable.

| Sample | $VRX10^{14}$ (Aged) |
| --- | --- |
| Example I | 3.6 |
| Example II | 3.7 |
| Conventional batch process (1 mole ZnO:2 moles pentaerythritol) | 0.8* |
| Physical blend (1 mole ZnO:2 moles pentaerythritol) | ** |

*failed at 8 weeks
**not measurable

Example V (Comparative)

Stabilizer systems based on the products of Examples I and II, and conventional zinc oxide/pentaerythritol batch products and physical blends as used in Example III, were added via compounding into PVC resin. Samples were formed of blended resin, and the samples were then subjected to dynamic thermal stability at 200° C. Compositions stabilized with the chemical products of Examples I and II displayed superior results as compared to compositions stabilized with conventional zinc oxide/pentaerythritol products.

| A. Before Humidity Aging | Minutes To Failure |
|---|---|
| Example I | 60 |
| Example II | 60 |
| Conventional batch process (1 mole ZnO:2 moles pentaerythritol) | 40 |
| Physical blend (1 mole ZnO:2 moles pentaerythritol) | 35 |

| B. After Humidity Aging | Minutes To Failure |
|---|---|
| Example I | 40 |
| Example II | 40 |
| Conventional batch process (1 mole ZnO:2 moles pentaerythritol) | 15 |
| Physical blend (1 mole ZnO:2 moles pentaerythritol) | 13 |

It will be understood that the method of the invention has been shown and described with respect to specific embodiments thereof, and other variations and modifications of the specific methods herein shown and described will be apparent to those skilled in the art all within the intended spirit and scope of the invention. Accordingly, the patent is not to be limited in scope and effect to the specific embodiments herein shown and described nor in any other way that is inconsistent with the extent to which the progress in the art has been advanced by the invention.

What is claimed:

1. A process for the preparation of a zinc oxide/pentaerythritol chemical product comprising the steps of:
   (i) providing a continuous processor having a raw material feed zone, a reaction zone, and a discharge zone;
   (ii) feeding zinc oxide and pentaerythritol into said product feed zone and providing a raw material mixture comprising said zinc oxide and said pentaerythritol, said raw material mixture comprising from about 1.7 to about 2.3 moles of said pentaerythritol for about every 1 mole of said zinc oxide;
   (iii) maintaining a melt temperature of from about 185° C. to about 245° C. in said reaction zone;
   (iv) maintaining a temperature of from about 185° C. to about 245° C. in said discharge zone;
   (v) transporting said raw material mixture into said reaction zone and maintaining a residence time for the raw material mixture in the reaction zone of from about 10 to about 60 seconds so as to provide a reacted chemical product;
   (vi) transporting said chemical product into said discharge zone; and
   (vii) removing said chemical product from said discharge zone.

2. A process as set forth in claim 1 including the step of venting volatile by-products produced by the reaction of said zinc oxide with said pentaerythritol.

3. A process as set forth in claim 2 wherein said venting occurs in said discharge zone.

4. A process as set forth in claim 2 wherein said venting occurs in a separate venting zone located between said reaction zone and said discharge zone.

5. A process as set forth in claim 2 wherein said venting occurs in said reaction zone.

6. A process as set forth in claim 1 including a Step (viii) of cooling and granulating said chemical product.

7. A process as set forth in claim 6 wherein said Step (viii) is conducted using a unit selected from the group consisting of a chilled roll flaker and a chilled belt flaker.

8. A process as set forth in claim 1 wherein prior to said Step (ii) said zinc oxide and said pentaerythritol are preblended.

9. A process as set forth in claim 1 wherein said product feed zone includes one or more automatic feeders for supplying mixed zinc oxide and pentaerythritol at the desired ratio to said reaction zone.

10. A process as set forth in claim 1 wherein the zinc oxide and pentaerythritol reside in said reaction zone and said discharge zone a minimum of about 70 seconds.

11. A zinc oxide/pentaerythritol chemical product made in accordance with the process of claim 1.

12. A zinc oxide/pentaerythritol chemical product that provides a stabilizer system that displays a retained volume resistivity in PVC resin after aging for 26 weeks at 70% relative humidity and 70° C. pursuant to test procedure ASTM D257(1994) of at least $1.0 \times 10^{14}$ Ohm-cm made by the process of claim 1.

13. A zinc oxide/pentaerythritol chemical product made by a continuous melt process, said continuous melt process comprises the process of feeding zinc oxide and pentaerythritol into the product feed zone of a continuous processor to provide a raw material mixture consisting essentially of said zinc oxide and said pentaerythritol, said raw material mixture consisting essentially of from about 1.7 to about 2.3 moles of said pentaerythritol for about every 1 mole of said zinc oxide, transporting said raw material mixture into the reaction zone of the continuous processor with the reaction zone providing a melt temperature of from about 185° C. to about 245° C. such that said raw material mixture maintains a residence time in said reaction zone of from about 10 to about 60 seconds for said raw material mixture so as to provide a reacted zinc oxide/pentaerythritol chemical product, and transporting said chemical product into the discharge zone of the continuous processor.

14. A zinc oxide/pentaerythritol chemical product as set forth in claim 13 wherein said continuous processor of said continuous melt process comprises a piece of equipment selected from the group consisting of a single screw extruder, a twin screw extruder, a continuous mixer, a melt processor and a co-kneader.

* * * * *